United States Patent

Krüger et al.

(10) Patent No.: US 6,194,443 B1
(45) Date of Patent: Feb. 27, 2001

(54) AMINOPHENOL DERIVATIVES WITH FUNGICIDAL PROPERTY

(75) Inventors: Bernd-Wieland Krüger, Bergisch Gladbach; Heinz-Wilhelm Dehne, Bonn; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/284,225

(22) PCT Filed: Oct. 2, 1997

(86) PCT No.: PCT/EP97/05430

§ 371 Date: Apr. 9, 1999

§ 102(e) Date: Apr. 9, 1999

(87) PCT Pub. No.: WO98/16522

PCT Pub. Date: Apr. 23, 1998

(30) Foreign Application Priority Data

Oct. 15, 1996 (DE) .............................. 196 42 529

(51) Int. Cl.⁷ .................. A61K 31/54; A61K 31/38; C07D 333/02; C07D 315/00; C07D 213/00
(52) U.S. Cl. .................. 514/357; 514/460; 514/448; 549/29; 549/65; 549/72; 549/74; 549/76; 549/78; 546/1
(58) Field of Search .................... 514/357, 448, 514/460; 549/29, 65, 74, 76, 78, 72; 546/1

(56) References Cited

U.S. PATENT DOCUMENTS

| 4,647,583 | 3/1987 | Takahashi et al. ............ 514/482 |
| 4,647,584 | 3/1987 | Takahashi et al. ............ 514/485 |
| 4,939,170 | 7/1990 | Kruger et al. ............ 514/483 |
| 5,059,623 | 10/1991 | Kruger et al. ............ 514/613 |
| 5,260,474 | 11/1993 | Kruger ............ 560/25 |
| 5,371,271 | 12/1994 | Kruger et al. ............ 560/136 |
| 5,492,931 | 2/1996 | Krueger et al. ............ 514/613 |
| 5,534,653 | 7/1996 | Wagner et al. ............ 564/32 |
| 5,565,490 | 10/1996 | Wagner et al. ............ 514/484 |
| 5,821,246 | 10/1998 | Brown et al. ............ 514/253 |

FOREIGN PATENT DOCUMENTS

| 2040175 | 2/1972 | (DE) . |
| 195 04 599 | 8/1996 | (DE) . |
| 116409 | * 8/1984 | (EP) . |
| 1350528 | 4/1974 | (GB) . |

OTHER PUBLICATIONS

J. Pharm. Science, vol. 79, Jan. 1990, pp. 66–73.
J. Chem. Soc (month unavailable) 1961, pp.1863–1879.

* cited by examiner

Primary Examiner—Richard L. Raymond
Assistant Examiner—Sudhaker B. Patel
(74) Attorney, Agent, or Firm—Joseph C. Gil

(57) ABSTRACT

The present invention pertains to new aminophenol derivatives of the following general formula (1), their preparation and their use as fungicides.

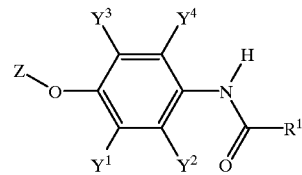

(1)

wherein $Y^1$, $Y^2$, $Y^3$, $Y^4$, $R^1$, and Z are as defined in the description.

8 Claims, No Drawings

AMINOPHENOL DERIVATIVES WITH FUNGICIDAL PROPERTY

TECHNICAL FIELD OF THE INVENTION

The invention relates to novel arninophenol derivatives, to a process for their preparation and to their use as fungicides.

BACKGROUND OF THE INVENTION

It is already known that certain aminophenol derivatives have fungicidal activity (compare, for example, EP-A 293718).

However, the activity of these prior-art compounds, in particular at low application rates and concentrations, is not entirely satisfactory in all areas of use.

DETAILED DESCRIPTION OF THE INVENTION

This invention, accordingly, provides the novel arninophenol derivatives of the general formula (I)

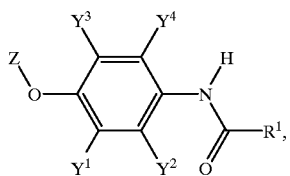

(I)

in which $Y^1$, $Y^2$, $Y^3$ and $Y^4$ independently of one another each represent hydrogen, halogen, alkyl, halogenoalkyl, alkoxy, halogenoalkoxy, alkylthio or halogenoalkylthio, $R^1$ represents in each case optionally substituted alkyl, alkenyl, aryl, cycloalkyl, cycloalkenyl or heterocyclyl and Z represents a grouping

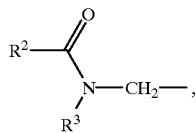

in which $R^2$ represents alkyl, alkoxy or alkylthio, each of which is optionally interrupted by oxygen atoms, and $R^3$ represents alkyl which is optionally interrupted by oxygen atoms, or Z represents a grouping

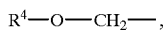

in which $R^4$ represents alkyl which is optionally interrupted by oxygen atoms, or Z represents a grouping

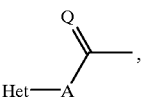

in which

Het represents optionally substituted heterocyclyl,

A represents a single bond, oxygen, sulphur, alkanediyl or represents

where $R^5$ represents hydrogen or alkyl, and

Q represents oxygen or sulphur.

In the definitions, the saturated or unsaturated hydrocarbon chains, such as alkyl, alkanediyl, alkenyl or alkinyl, including those in combination with hetero atoms, such as in alkoxy, alkylthio or alkylarnino, are in each case straight-chain or branched. If the hydrocarbon chains are interrupted by oxygen atoms, the oxygen atoms are not in a terminal position, and two oxygen atoms in a chain are in each case interrupted by at least two carbon atoms.

Halogen generally represents fluorine, chlorine, bromine or iodine, preferably represents fluorine, chlorine or bromine and in particular represents fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a hetero atom, i.e. an atom other than carbon. If the ring contains a plurality of hetero atoms, these can be identical or different. Preferred hetero atoms are oxygen, nitrogen or sulphur. If the ring contains a plurality of oxygen atoms, these are not adjacent. If appropriate, the cyclic compounds form, together with other carbocyclic or heterocyclic fused-on or bridged rings, a polycyclic ring systemn Preference is given to mono- or bicyclic ring systems, in particular to mono- or bicyclic aromatic ring systems.

Cycloalkyl represents saturated, carbocyclic compounds which, if appropriate, form a polycyclic ring system with other carbocyclic fused-on or bridged rings.

Cycloalkenyl represents carbocyclic cyclic compounds which contain at least one double bond and which form, if appropriate, a polycyclic ring system with other carbocyclic fused-on or bridged rings.

Furthermore, it has been found that the novel compounds of the general formula (I) are obtained when a) hydroxyl compounds of the general formula (II)

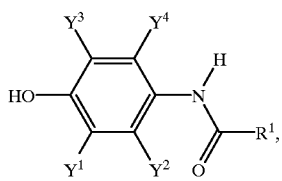

in which
R$^1$, Y$^1$, Y$^2$, Y$^3$ and Y$^4$ are each as defined above,
are reacted with a halogen compound of the general formula (III)

    (III), in which
Z is as defined above and
X$^1$ represents halogen,
if appropriate in the presence of an acid acceptor and if appropriate in the presence of a diluent, or when b)
amino compounds of the general formula (IV)

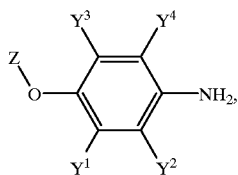

in which
Y$^1$, Y$^2$, Y$^3$, Y$^4$ and Z are each as defined above,
are reacted with a carboxylic acid derivative of the general formula (V)

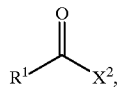

in which
R$^1$ is as defined above and
X$^2$ represents halogen or

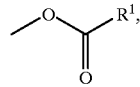

if appropriate in the presence of an acid acceptor and if appropriate in the presence of a diluent.

Finally, it has been found that the novel compounds of the general formula (I) have very strong fungicidal activity.

If appropriate, the compounds according to the invention are present as mixtures of various possible isomeric forms, in particular of stereoisomers, such as, for example, E and Z, threo and erythro, and also optical isomers. What is claimed are both the E and the Z isomers, and also the threo and erythro and the optical isomers, and any mixtures of these isomers.

The invention preferably provides compounds of the formula (I) in which
Y$^1$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms,
Y$^2$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms,
Y$^3$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms,
Y$^4$ represents hydrogen, halogen, alkyl, alkoxy, alkylthio having in each case 1 to 4 carbon atoms, halogenoalkyl, halogenoalkoxy, halogenoalkylthio having in each case from 1 to 3 carbon atoms and 1 to 5 identical or different halogen atoms,
where at least two of the radicals Y$^1$ to Y$^4$ represent halogen,
R$^1$ represents in each case optionally mono- to pentasubstituted alkyl or alkenyl having in each case 4 to 10 carbon atoms, and the possible substituents are preferably selected from the following list: halogen, alkoxy having 1 to 4 carbon atoms, alkylthio having 1 to 4 carbon atoms, halogenoalkoxy having 1 to 2 carbon atoms and 1 to 5 halogen atoms, halogenoalkylthio having 1 to 2 carbon atoms and 1 to 5 halogen atoms or optionally halogen- or alkyl-substituted cycloalkyl having 3 to 6 carbon atoms, where the carbon atom which is attached to the carbonyl group does not carry a hydrogen atom, or
R$^1$ represents in each case optionally mono- to pentasubstituted cycloalkyl or cycloalkenyl having in each case 3 to 12 carbon atoms, and the possible substituents are preferably selected from the following list: halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 halogen atoms, halogenoalkoxy having 1 to 2 carbon atoms and 1 to 5 halogen atoms, halogenoalkylthio having 1 to 2 carbon atoms and 1 to 5 halogen atoms or optionally halogen- or alkyl-substituted cycloalkyl having 3 to 6 carbon atoms, and
Z represents a grouping

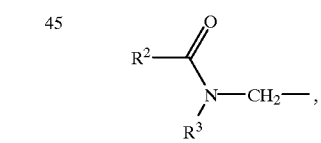

in which
R$^2$ represents alkyl, alkoxy or alkylthio having 1 to 8 carbon atoms, each of which is optionally interrupted by 1 to 2 oxygen atoms, and
R$^3$ represents alkyl having 1 to 8 carbon atoms which is optionally interrupted by 1 to 2 oxygen atoms, or
Z represents a grouping

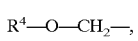

in which
R$^4$ represents alkyl having 1 to 8 carbon atoms which is optionally interrupted by 1 to 2 oxygen atoms.

The present invention also preferably provides compounds of the formula (I) in which
Y$^1$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^2$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^3$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^4$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, where at least two of the radicals $Y^1$ to $Y^4$ represent halogen, $R^1$ represents in each case optionally mono- to pentasubstituted alkyl or alkenyl having in each case 4 to 10 carbon atoms, and the possible substituents are preferably selected from the following list: halogen, alkoxy having 1 to 4 carbon atoms, alkylthio having 1 to 4 carbon atoms, halogenoalkoxy having 1 to 2 carbon atoms or 1 to 5 halogen atoms, halogenoalkylthio having 1 to 2 carbon atoms and 1 to 5 halogen atoms or optionally halogen- or alkyl-substituted cycloalkyl having 3 to 6 carbon atoms, where the carbon atom which is attached to the carbonyl group does not carry a hydrogen atom, or $R^1$ represents in each case optionally mono- to pentasubstituted cycloalkyl or cycloalkenyl having in each case 3 to 12 carbon atoms, and the possible substituents are preferably selected from the following list: halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 halogen atoms, halogenoalkoxy having 1 to 2 carbon atoms and 1 to 5 halogen atoms, halogenoalkylthio having 1 to 2 carbon atoms and 1 to 5 halogen atoms or optionally halogen- or alkyl-substituted cycloalkyl having 3 to 6 carbon atoms, and Z represents a grouping

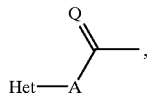

in which

Het represents heterocyclyl having 3 to 7 ring members, 1 to 3 of which are in each case identical or different hetero atoms (in particular nitrogen, oxygen and/or sulphur), which is optionally mono- to trisubstituted by halogen, alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl having in each case 1 to 4 carbon atoms, A represents a single bond, oxygen, sulphur, alkanediyl having 1 to 2 carbon atoms, or represents

where $R^5$ represents hydrogen or alkyl having 1 to 4 carbon atoms, and

Q represents oxygen or sulphur.

The invention in particular relates to compounds of the formula (I) in which $Y^1$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^2$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^3$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^4$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, where at least two of the radicals $Y^1$ to $Y^4$ in each case represent fluorine, chlorine or bromine, $R^1$ represents 1-methyl-propyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-imethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the abovementioned alkyl radicals are optionally substituted by 1 to 3 halogen atoms, preferably fluorine, chlorine or bromine, or $R^1$ represents 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2 -pentenyl, 4-methyl-2-pentenyl, 1-methyl-3-pentenyl, 2-niethyl-3-pentenyl, 3-methyl-3-pentenyl, 4-methyl-3-pentenyl, 1-methyl4-pentenyl, 2-methyl-4-pentenyl, 3-methylpentenyl, 4-methylApentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-1-methyl-2-propenyl, 1-ethyl-2-methyl-1-propenyl and 1-ethyl-2-methyl-2-propenyl, where the abovementioned alkyl radicals are optionally substituted by 1 to 3 halogen atoms, preferably fluorine, chlorine or bromine, or $R^1$ represents cyclopropyl, cyclobutyl, cyclopentyl, cyclohexyl, cycloheptyl, 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl, where the abovementioned radicals are optionally substituted by 1 to 3 halogen atoms, preferably chlorine, fluorine or bromine, and/or methyl or ethyl, or $R^1$ represents bicyclo-[2.2 1]-hex-5-yl, bicyclo-[2.2.1]-hept-2-yl, bicycylo-[2.2.2]-oct-2-yl, bicyclo-[3.2.1]-oct-6-yl, bicyclo-[3.2.2]-non-6-yl, bicyclo-[4.2.2]-dec-7-yl, bicyclo-[3.1.0]-hex-1-yl, bicyclo-[4.1.0]-hept-1-yl, bicyclo-[4.3.0]-non-1-yl, bicyclo-[4.4.0]-dec-1-yl, particularly preferably represents 5-methyl-bicyclo-[2.1.1]-hex-5-yl, 2-methyl-bicyclo-[2.2.1]-hept-2-yl, 2-methyl-bicyclo-[2.2.2]-oct-2-yl, 6-methyl-bicyclo-[3.2.1]-oct-6-yl, 6-methyl-bicyclo-[3.2.2]-non-6-yl, 7-methyl-bicyclo-[4.2.2]-dec-7-yl, 1-methyl-bicyclo-[3.1.0]-hex-1-yl, 1-methyl-bicyclo-[4.1.0]-hept-1-yl, 1-methyl-bicyclo-[4.3.0]-non- 1-yl, 1-methyl-bicyclo-[4.4.0]-dec-1-yl, 2-methyl-bicyclo-[3.1.0]-hex-1-yl, 2-methyl-bicyclo-[4.1.0]-hept-1-yl, 2-methyl-bicyclo-[4.3.0]-non-1-yl, 2-methyl-bicyclo-[4.4.0]-dec-1-yl, bicyclo-[2.2.1]-hept-2-en-5-yl, bicyclo-[2.2.2]-oct-2-en-5-yl, bicyclo-[4.2.2]-dec-7-en-2-yl, bicyclo-14.3.0]-non-7 -en-1-yl, bicyclo-[4.4.0]dec-3-en-1-yl, bicyclo-[4.1.0]-hept-3-en-1-yl, 5-methyl-bicyclo-[2.2.1]-hept-2-en-5-yl, 5-methyl-bicyclo-[2.2.2]-oct-2-en-5-yl, 2-methyl-bicyclo-[4.2.2]-dec-7-en-2-yl, 2-methyl-bicyclo-[4.3.0]-non-7-en-1-yl, 2-methyl-bicyclo-[4.4.0]-dec-3-en-1-yl and 2-methyl-bicyclo-[4.1.0]-hept-3-en-1-yl, Z represents a grouping

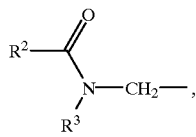

in which $R^2$ represents alkyl or alkoxy having 1 to 6 carbon atoms, each of which is optionally interrupted by an oxygen atom, and $R^3$ represents alkyl having 1 to 6 carbon atoms which is optionally interrupted by an oxygen atom, or Z represents a grouping $R^4—O—CH_2—$, in which $R^4$ represents alkyl having 1 to 6 carbon atoms which is optionally interrupted by an oxygen atom If $R^1$ is optionally substituted alkyl it is substituted in particular in such a way that the carbon atom which is attached to the carbonyl group does not carry a hydrogen atom.

The invention also in particular relates to compounds of the formula (I) in which $Y^1$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^2$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^3$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^4$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthlio, where at least two of the radicals $Y^1$ to $Y^4$ in each case represent fluorine, chlorine or bromine, $R^1$ represents 1-methyl-propyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-imethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the abovementioned alkyl radicals are optionally substituted by 1 to 3 halogen atoms, preferably fluorine, chlorine or bromine, or $R^1$ represents 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1 -butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-niethyl-3-pentenyl, 3-methyl-3-pentenyl, 4-methyl-3-pentenyl, 1-methyl4-pentenyl, 2-methyl-4-pentenyl, 3-methylpentenyl, 4-methylApentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-1-methyl-2-propenyl, 1-ethyl-2-methyl-1-propenyl and 1-ethyl-2-methyl-2-propenyl, where the abovementioned alkyl radicals are optionally substituted by 1 to 3 halogen atoms, preferably fluorine, chlorine or bromine, or $R^1$ represents cyclopropyl, cyclobutyl, cyclopentyl, cyclohexyl, cycloheptyl, 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl, where the abovementioned radicals are optionally substituted by 1 to 3 halogen atoms, preferably chlorine, fluorine or bromine, and/or methyl or ethyl, or $R^1$ represents bicyclo-[2.2 1]-hex-5-yl, bicyclo-[2.2.1]-hept-2-yl, bicycylo-[2.2.2]-oct-2-yl, bicyclo-[3.2.1]-oct-6-yl, bicyclo-[3.2.2]-non-6-yl, bicyclo-[4.2.2]-dec-7-yl, bicyclo-[3.1.0]-hex-1-yl, bicyclo-[4.1.0]-hept-1-yl, bicyclo-[4.3.0]-non-1-yl, bicyclo-[4.4.0]-dec-1-yl, particularly preferably represents 5-methyl-bicyclo-[2.1.1]-hex-5-yl, 2-methyl-bicyclo-[2.2.1]-hept-2-yl, 2-methyl-bicyclo-[2.2.2]-oct-2-yl, 6-methyl-bicyclo-[3.2.1]-oct-6-yl, 6 -methyl-bicyclo-[3.2.2]-non-6-yl, 7-methyl-bicyclo-[4.2.2]-dec-7-yl, 1-methyl-bicyclo-[3.1.0]-hex-1-yl, 1-methyl-bicyclo-[4.1.0]-hept-1-yl, 1-methyl-bicyclo-[4.3.0]-non- 1-yl, 1-methyl-bicyclo-[4.4.0]-dec-1-yl, 2-methyl-bicyclo-[3.1.0]-hex-1-yl, 2-methyl-bicyclo-[4.1.0]-hept-1-yl, 2-methyl-bicyclo-[4.3.0]-non-1-yl, 2-methyl-bicyclo-[4.4.0]-dec-1-yl, bicyclo-[2.2.1]-hept-2-en-5-yl, bicyclo-[2.2.2]-oct-2-en-5-yl, bicyclo-[4.2.2]-dec-7-en-2-yl, bicyclo-14.3.0]-non-7-en-1-yl, bicyclo-[4.4.0]dec-3-en-1-yl, bicyclo-[4.1.0]-hept-3-en-1-yl, 5-methyl-bicyclo-[2.2.1]-hept-2-en-5-yl, 5-methyl-bicyclo-[2.2.2]-oct-2-en-5-yl, 2-methyl-bicyclo-[4.2.2]-dec-7-en-2-yl, 2-methyl-bicyclo-[4.3.0]-non-7-en-1-yl, 2-methyl-bicyclo-[4.4.0]-dec-3-en-1-yl and 2-methyl-bicyclo-[4.1.0]-hept-3-en-1-yl, Z represents a grouping

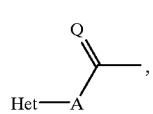

in which

Het represents heterocyclyl having 3 to 7 ring members, 1 to 3 of which are in each case identical or different hetero atoms (in particular nitrogen, oxygen and/or sulphur), which is optionally mono- to trisubstituted by halogen, alkyl, alkoxy, alkylthio, alkylsulphinyl, alkylsulphonyl, halogenoallyl, halogenoalkoxy, halogenoalkylthio, halogenoalkylsulphinyl or halogenoalkylsulphonyl having in each case 1 to 4 carbon atoms, A represents the single bond, oxygen, sulphur, methylene or represents

where $R^5$ represents hydrogen, methyl or ethyl, and

Q represents oxygen or sulphur.

If $R^1$ is optionally substituted alkyl, it is substituted in particular in such a way that the carbon atom which is attached to the carbonyl group does not carry a hydrogen atom.

Very particular preference is given to compounds of the formula (I) in which $Y^1$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^2$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^3$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^4$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, where in each case at least two of the radicals $Y^1$ to $Y^4$ represent fluorine, chlorine or bromine, $R^1$ represents 1-methyl-propyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-imethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the abovementioned alkyl radicals are optionally substituted by 1 to 3 halogen atoms, preferably fluorine, chlorine or bromine, or $R^1$ represents 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-niethyl-3-pentenyl, 3-methyl-3-pentenyl, 4-methyl-3-pentenyl, 1-methyl4-pentenyl, 2-methyl-4-pentenyl, 3-methylpentenyl, 4-methylApentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1- butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-1-methyl-2-propenyl, 1-ethyl-2-methyl-1-propenyl and 1-ethyl-2-methyl-2-propenyl, where the abovementioned alkyl radicals are optionally substituted by 1 to 3 halogen atoms, preferably fluorine, chlorine or bromine, or $R^1$ represents cyclopropyl, cyclobutyl, cyclopentyl, cyclohexyl, cycloheptyl, 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl, where the abovementioned radicals are optionally substituted by 1 to 3 halogen atoms, preferably chlorine, fluorine or bromine, and/or methyl or ethyl, or $R^1$ represents bicyclo-[2.2 1]-hex-5-yl, bicyclo-[2.2.1]-hept-2-yl, bicycylo-[2.2.2]-oct-2-yl, bicyclo-[3.2.1]-oct-6-yl, bicyclo-[3.2.2]-non-6-yl, bicyclo-[4.2.2]-dec-7-yl, bicyclo-[3.1.0]-hex-1-yl, bicyclo-[4.1.0]-hept-1-yl, bicyclo-[4.3.0]-non-1-yl, bicyclo-[4.4.0]-dec-1-yl, particularly preferably represents 5-methyl-bicyclo-[2.1.1]-hex-5-yl, 2-methyl-bicyclo-[2.2.1]-hept-2-yl, 2-methyl-bicyclo-[2.2.2]-oct-2-yl, 6-methyl-bicyclo-[3.2.1]-oct-6-yl, 6-methyl-bicyclo-[3.2.2]-non-6-yl, 7-methyl-bicyclo-[4.2.2]-dec-7-yl, 1-methyl-bicyclo-[3.1.0]-hex-1-yl, 1-methyl-bicyclo-[4.1.0]-hept-1-yl, 1-methyl-bicyclo-[4.3.0]-non- 1-yl, 1-methyl-bicyclo-[4.4.0]-dec-1-yl, 2-methyl-bicyclo-[3.1.0]-hex-1-yl, 2-methyl-bicyclo-[4.1.0]-hept-1-yl, 2-methyl-bicyclo-[4.3.0]-non-1-yl, 2-methyl-bicyclo-[4.4.0]-dec-1-yl, bicyclo-[2.2.1]-hept-2-en-5-yl, bicyclo-[2.2.2]-oct-2-en-5-yl, bicyclo-[4.2.2]-dec-7-en-2-yl, bicyclo-14.3.0]-non-7-en-1-yl, bicyclo-[4.4.0]dec-3-en-1-yl, bicyclo-[4.1.0]-hept-3-en-1-yl, 5-methyl-bicyclo-[2.2.1]-hept-2-en-5-yl, 5-methyl-bicyclo-[2.2.2]-oct-2-en-5-yl, 2-methyl-bicyclo-[4.2.2]-dec-7-en-2-yl, 2-methyl-bicyclo-[4.3.0]-non-7-en-1-yl, 2-methyl-bicyclo-[4.4.0]-dec-3-en-1-yl and 2-methyl-bicyclo-[4.1.0]-hept-3-en-1-yl, Z represents a grouping

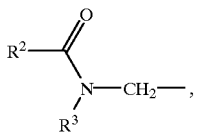

in which
$R^2$ represents methyl, ethyl, n- or i-propyl, n-, i-, s- or t-butyl, methoxyethyl, methoxy, ethoxy, n- or i-propoxy or methoxyethoxy and
$R^3$ represents methyl, ethyl, n- or i-propyl, n-, i-, s- or t-butyl or methoxyethyl or Z represents a grouping $R^4$—O—CH$_2$—, in which $R^4$ represents methyl, ethyl, n- or i-propyl, n-, i-, s- or t-butyl or methoxyethyl.

If $R^1$ represents optionally substituted alkyl, it is substituted in particular in such a way that the carbon atom which is attached to the carbonyl group does not carry a hydrogen atom.

Very particular preference is also given to compounds of the formula (I) in which $Y^1$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^2$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^3$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, $Y^4$ represents hydrogen, fluorine, chlorine, bromine, methyl, methoxy, ethoxy, trifluoromethyl, difluoromethyl, fluoromethyl, fluorochloromethyl, difluoromethoxy, trifluoromethoxy, difluorochloromethoxy, where in each case at least two of the radicals $Y^1$ to $Y^4$ represent fluorine, chlorine or bromine, $R^1$ represents 1-methyl-propyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-imethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the abovementioned alkyl radicals are optionally substituted by 1 to 3 halogen atoms, preferably fluorine, chlorine or bromine, or $R^1$ represents 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-niethyl-3-pentenyl, 3-methyl-3-pentenyl, 4-methyl-3-pentenyl, 1-methyl4-pentenyl, 2-methyl-4-pentenyl, 3-methylpentenyl, 4-methylApentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-1-methyl-2-propenyl, 1-ethyl-2-methyl-1-propenyl and 1-ethyl-2-methyl-2-propenyl, where the abovementioned alkyl radicals are optionally substituted by 1 to 3 halogen atoms, preferably fluorine, chlorine or bromine, or $R^1$ represents cyclopropyl, cyclobutyl, cyclopentyl, cyclohexyl, cycloheptyl, 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl, where the abovementioned radicals are optionally substituted by 1 to 3 halogen atoms, preferably chlorine, fluorine or bromine, and/or methyl or ethyl, or $R^1$ represents bicyclo-[2.2 1]-hex-5-yl, bicyclo-[2.2.1]-hept-2-yl, bicycylo-[2.2.2]-oct-2-yl, bicyclo-[3.2.1]-oct-6-yl, bicyclo-[3.2.2]-non-6-yl, bicyclo-[4.2.2]-dec-7-yl, bicyclo-[3.1.0]-hex-1-yl, bicyclo-[4.1.0]-hept-1-yl, bicyclo-[4.3.0]-non-1-yl, bicyclo-[4.4.0]-dec-1-yl, particularly preferably represents 5-methyl-bicyclo-[2.1.1]-hex-5-yl, 2-methyl-bicyclo-[2.2.1]-hept-2-yl, 2-methyl-bicyclo-[2.2.2]-oct-2-yl, 6-methyl-bicyclo-[3.2.1]-oct-6-yl, 6-methyl-bicyclo-[3.2.2]-non-6-yl, 7-methyl-bicyclo-[4.2.2]-dec-7-yl, 1-methyl-bicyclo-[3.1.0]-hex-1-yl, 1-methyl-bicyclo-[4.1.0]-hept-1-yl, 1-methyl-bicyclo-[4.3.0]-non- 1-yl, 1-methyl-bicyclo-[4.4.0]-dec-1-yl, 2-methyl-bicyclo-[3.1.0]-hex-1-yl, 2-methyl-bicyclo-[4.1.0]-hept-1-yl, 2-methyl-bicyclo-[4.3.0]-non-1-yl, 2-methyl-bicyclo-[4.4.0]-dec-1-yl, bicyclo-[2.2.1]-hept-2-en-5-yl, bicyclo-[2.2.2]-oct-2-en-5-yl, bicyclo-[4.2.2]-dec-7-en-2-yl, bicyclo-14.3.0]-non-7-en-1-yl, bicyclo-[4.4.0]dec-3-en-1-yl, bicyclo-[4.1.0]-hept-3-en-1-yl, 5-methyl-bicyclo-[2.2.1]-hept-2-en-5-yl, 5-methyl-bicyclo-[2.2.2]-oct-2-en-5-yl, 2-methyl-bicyclo-[4.2.2]-dec-7-en-2-yl, 2-methyl-bicyclo-[4.3.0]-non-7-en-1-yl, 2-methyl-bicyclo-[4.4.0]-dec-3-en-1-yl and 2-methyl-bicyclo-[4.1.0]-hept-3-en-1-yl, Z represents a grouping

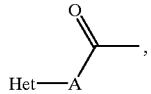

in which

Het represents furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofiuyl, perhydropyranyl, pyrlolidinyl, piperidinyl or morpholinyl, optionally mono- to trisubstituted by fluorine, chlorine, bromine, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethyl, trifluoromethoxy, difluoromethoxy, difluorochloromethoxy, trifluoromethylthio, difluoromethylthio or difluorochloromethylthio, and A represents the single bond, oxygen, sulphur, methylene or represents

If $R^1$ represents optionally substituted alkyl, it is substituted in particular in such a way that the carbon atom which is attached to the carbonyl group does not carry a hydrogen atom.

Of very particular interest are compounds of the formula (I) in which $R^1$ and Z are each as defined above and in which
$Y^1$ and $Y^2$ represent chlorine,
$Y^3$ represents hydrogen or chlorine and
$Y^4$ represents hydrogen.

Furthermore, of very particular interest are compounds of the formula (I) in which
$R^1$ and Z are each as defined above and in which
$Y^1$ and $Y^4$ represent chlorine and
$Y^2$ and $Y^3$ represent hydrogen.

Likewise, of very particular interest are compounds in which
$Y^1, Y^2, Y^3, Y^4$ and Z are each as defined above and in which
$R^1$ represents cyclopentyl, cyclohexyl, bicyclo-2,2,1-heptyl or bicyclo-2,2,2-octyl, each of which is substituted at the linking point by methyl, ethyl, chlorine or bromine, or
represents cyclopropyl which is substituted at at least 2 positions by chlorine and on each of the other three free positions optionally by methyl or ethyl, or
represents t-butyl which is optionally mono- to trisubstituted by fluorine or chlorine.

The abovementioned general or preferred radical definitions apply both to the end products of the formula (I) and also, correspondingly, to the starting materials or intermediates required in each case for the preparation.

These radical definitions can be combined with each other as desired, i.e. including combinations between the abovementioned ranges of preferred compounds.

The formula (II) provides a general definition of the hydroxyl compounds required as starting materials for carrying out the process a) according to the invention. In this formula (II), $R^1, Y^1, Y^2, Y^3$ and $Y^4$ each preferably or in particular have those meanings which have already been mentioned in connection with the description of the compounds of the formula (I) according to the invention as being preferred or as being particularly preferred for $R^1, Y^1, Y^2, Y^3$ and $Y^4$.

The starting materials of the formula (II) are known and/or can be prepared by processes known per se (cf., for example, EP-A 293718, EP-A 339418, EP-A 653418, EP-A 653417, DE-A 19504599).

The formula (III) provides a general definition of the halogen compounds furthermore required as starting materials for carrying out the process a) according to the invention. In this formula (III) Z preferably or in particular has those meaning which have already been mentioned in connection with the description of the compounds of the formula (I) according to the invention as being preferred or as being particularly preferred for Z. $X^1$ represents halogen, and preferably represents chlorine or bromine.

The halogen compounds of the general formula (III) are known and/or can be prepared by processes known per se (cf., for example, DE-A 2119518, DE-A 2040175, J. Pharm. Sci., 79, 1, 1990, 66–73).

The formula (IV) provides a general definition of the amino compounds required as starting materials for carrying out the process b) according to the invention. In this formula (IV), $Y^1$, $Y^2$, $Y^3$, $Y^4$ and Z each preferably or in particular have those meanings which have already been mentioned in connection with the description of the compounds of the formula (I) according to the invention as being preferred or as being particularly preferred for $Y^1$, $Y^2$, $Y^3$, $Y^4$ and Z.

Some of the amino compounds of the formula (IV) are known and have been described in the literature (compare, for example, J. Chem. Soc., 1961, 1863–1879 and WO-A 96-15118).

Novel and also part of the subject-matter of the present application are amino compounds of the formula (IV-a)

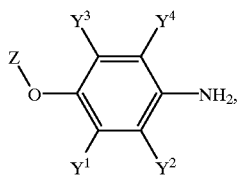

(IV-a)

in which
$y^1$, $Y^2$, $Y^3$, $Y^4$ and Z are each as defined above, but where at least two of the radicals $Y^1$, $Y^2$, $Y^3$ or $Y^4$ represent halogen.

The amino compounds of the formula (IV-a) are obtained (process c), when aminophenols of the general formula (VI)

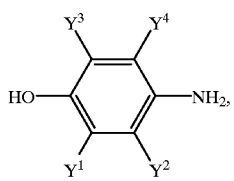

(VI)

in which
$Y^1$, $Y^2$, $Y^3$ and $Y^4$ are as defined above,
are reacted with a halogen compound of the general formula (III)

$$Z\text{—}X^1 \quad (III),$$

in which
Z is as defined above and
$X^1$ represents halogen,
if appropriate in the presence of an acid acceptor and if appropriate in the presence of a diluent.

The formula (VI) provides a general definition of the aminophenols required as starting materials for carrying out the process c) according to the invention. In this formula (VI), $Y^1$, $Y^2$, $Y^3$ and $Y^4$ each preferably and in particular have those meanings which have already been mentioned in connection with the description of the compounds of the formula (I) according to the invention as being preferred or as being particularly preferred for $Y^1$, $Y^2$, $Y^3$ and $Y^4$.

The aminophenols of the formula (VI) are known chemicals for synthesis.

The halogen compounds of the formula (III) furthermore required as starting materials for carrying out the process c) according to the invention have already been described in connection with the description of the process a) according to the invention.

Suitable diluents for carrying out the processes a), b) and c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric triamide; sulfoxides, such as dimethyl sulfoxide; or sulfones, such as sulfolane.

The processes a), b) and c) according to the invention are, if appropriate, carried out in the presence of a suitable acid acceptor. Suitable acid acceptors are all customary inorganic or organic bases. These preferably include alkaline earth metal or alkali metal hydroxides, acetates, carbonates, bicarbonates, such as, for example, sodium hydroxide, potassium hydroxide, sodium acetate, potassium acetate, calcium acetate, sodium carbonate, potassium carbonate, potassium bicarbonate or sodium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a), b) and c) according to the invention, the reaction temperatures can be varied within a relatively wide range. In general, the processes are carried out at temperatures from −50° C. to 150° C., preferably at temperatures from −10° C. to 120° C.

For carrying out the process a) according to the invention for preparing the compounds of the formula (I), generally 0.5 to 5 mol, preferably 0.8 to 2.5 mol, of halogen compound of the formula (III) are employed per mole of the hydroxyl compound of the formula (II).

For carrying out the process b) according to the invention for preparing the compounds of the formula (I), generally 0.5 to 5 mol, preferably 0.8 to 2.5 mol, of carboxylic acid derivative of the formula (V) are employed per mole of the amino compound of the formula (IV).

For carrying out the process c) according to the invention for preparing the compounds of the formula (IV-a), generally 0.5 to 5 mol, preferably 0.8 to 2.5 mol, of halogen compound of the formula (III) are employed per mole of the aminophenol of the formula (VI).

When carrying out the processes a), b) and c) according to the invention, the reaction temperatures can be varied within a relatively wide range. The processes are generally carried out at temperatures from −50° C. to 150° C., preferably at temperatures from −10° C. to 120° C.

The processes a), b) and c) according to the invention are generally carried out under atmospheric pressure. However, it is also possible to operate under elevated or reduced pressure—generally between 0.1 bar and 10 bar.

The practice of the reaction, the work-up and the isolation of the reaction products is carried out by known processes (cf. the Preparation Examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as non-limiting examples:

Xanthomonas species, such as, for example, *Xanthomonas campestris pv. oryzae;*
Pseudomonas species, such as, for example, *Pseudomonas syringae pv. lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Botrytis species. They also have strong in vitro activity. Furthermore, the compounds according to the invention may also be employed to increase the yield of crops.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations also mixed with known fungicides, bactericides, acaricides, nematicides or insecticides in order thus, for example, to broaden the spectrum of action or to prevent development of resistance. In many cases, synergistic effects are achieved, i.e. the activity of the mixture exceeds the activity of the individual components. Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticdiin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclornezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbain, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux rnixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procynudone, propamocarb, propanosine-sodium, propiconazole, propineb, pyrazophos, pyrifenox, pyrimethanil, pyroquilon, pyroxyfur, quinconazole, quintozene(PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4(trifluoromethyl)-phenyl]-methylene]-1H- 1,2,4-triazole-1-ethanol, (5RS,6RS)-6hydroxy-2,2,7,7-tetramethyl-5-( 1H- 1,2,4-triazol-1-yl)-3-octanone, (E)-α-(methoxyimino)-N-methyl-2-phenoxy-phenylacetamide, isopropyl {2-methyl-1-[[[1-(4-methylphenyl)ethyl]amino]carbonyl]propyl}-carbamate, 1-(2,4-dichlorophenyl)2-(1H-1,2,4-triazol-1-yl)ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H- 1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinole, 2',6'-dibromo-2-methyl4'-trifluoromethoxy-4'-trifluoro-methyl-1,3-thiazole-5-carboxanilide, 2,2-dichloro-N-[1 -(4chlorophenyl)ethyl]-1-ethyl-3-methyl-cyclopropane-carboxamide, 2,6-dichloro-5-(methylthio)-4-pyrimidinylthiocyanate, 2,6-dichloro-N-(4-trifluoromethylbenzyl)-benzamide, 2,6-dichloro-N-[[4-(trifluoromethyl)phenyl]methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy4O-(4-O-methyl-β-D-glycopyranosyl)-α-D-glucopyranosyl]-amino]4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)oxy]methyl]-benzamide, 3-(1,1 -dimethylpropyl-1-oxo-1H-indene-2-carbonitrile, 3-[2-(4-chlorophenyl)-5-ethoxy-3-isoxazolidinyl)-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4dioxaspiro[4.5]decane-2-methanamine, 8-hydroxyquinoline sulphate, 9H-xanthene-2-[(phenylamino)-carbonyl]-9-carboxylic hydrazide, bis-( 1 -methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4(1,1-dimethylpropyl)-phenyl-2-methylpropyl]-2,6-dimethyl-morpholine hydrochloride, ethyl [(4-chlorophenyl)-azo]-cyanoacetate,
potassium hydrogencarbonate,
methanetetrathiol, sodium salt,
methyl 1-(2,3-dihydro-2,2-dimethyl-1H-inden-1-yl)-1H-imidazole-5-carboxylate,
methyl N-(2,6dimethylphenyl)-N-(5-isoxazolylcarbonyl)-DL-alaninate,
methyl N-(chloroacetyl)-N-(2,6dimethylphenyl)-DL-alaninate,
N-(2,3-dichlorofhydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)4-methyl-3-nitro-benzenesulfonamide,
N-(4-cyclohexylphenyl)-1,4,5,6-tetrahydro-2-pyrirnidinamnine,
N-(4hexylphenyl)- 1,4,5,6-tetrahydro-2-pyrimidinarnine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-aminol-ethyl]-benzamide,
N-[3-chloro4,5-bis(2-propinyloxy)-phenyl]-N'-methoxy-methanimidamide,
N-formyl-N-hydroxy-DL-alanine, sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
  bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate,
dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate,
flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram
omethoate, oxamyl, oxydemethon M, oxydeprofos,
parathion A, parathion M, permethrin, phenthoate, phorate, phosalone, phosmet, phosphamidon, phoxim, pimicarb, pimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrirnidifen, pyriproxifen,
quinalphos,
salithion, sebufos, silafluofen, sulfotep, sulprofos,
tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth regulators.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound preparation, or the active compound itself, into the soil. The seed of the plants can also be treated.

In the treatment of parts of plants, the active compound concentrations in the use forms can be varied within a relatively wide range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed. In the treatment of the soil, active compound concentrations of from 0.00001 to 0.1% by weight, preferably from 0.0001 to 0.02% by weight, are required at the site of action.

PREPARATION EXAMPLES

Example 1

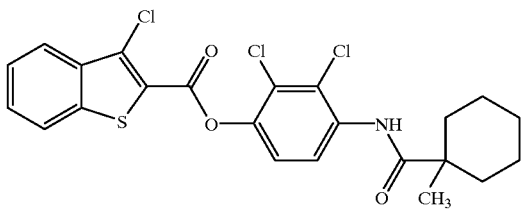

Process a)
2.1 g (0.007 mol) of 4-(1-methyl-cyclohexyl)-carbonylamino-2,3-dichlorophenol and 1 ml of (0.007 mol)

of triethylamine are dissolved in 30 ml of tetrahydrofuran. At 0° C., 1.61 g (0.007 mol) of 3-chlorobenzothiophene-2-carbonyl chloride, dissolved in 20 ml of tetrahydrofuran, are then added dropwise to the reaction mixture. The mixture is warmed to 20° C. and, to bring the reaction to completion, another 0.8 g (3.5 mmol) of carbonyl chloride are added. After the reaction has ended, the reaction mixture is poured into water and extracted repeatedly with ethyl acetate, the organic phase is dried over magnesium sulphate and concentrated under reduced pressure. The residue is chromatographed over silica gel using hexane/ethyl acetate/acetone (30:10:1). This gives 3.2 g (91% of theory) of 4-(1-methyl-cyclohexyl)-carbonylamino-2,3-dichlorophenyl 3-chlorobenzothiophene-2-carboxylate of melting point 108° C.

Example 2

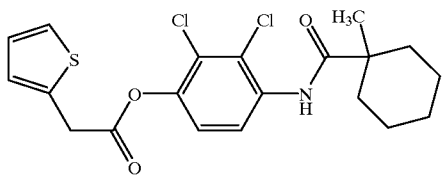

Process b)

About 50 mg of dimethylaminopyridine and 0.13 g (0.8273 mmol) of 1 -methylcyclohexanecarbonyl chloride are added successively to a solution of 0.25 g (0.8273 mmol) of 4-amino-2,3-dichlorophenyl thiophen-2-yl-acetate in 10 ml of pyridine, and the mixture is stirred for 18 hours. The reaction mixture is poured into 200 ml of water and extracted 3 times with 100 ml of ethyl acetate each time. The combined organic phases are washed twice with 50 ml of 1N hydrochloric acid each and once with 50 ml of water, dried over magnesium sulphate and concentrated under reduced pressure. The residue is chromatographed over silica gel using cyclohexane/ethyl acetate (6:1). This gives 0.14 g (40% of theory) of 2,3-dichloro4-[(1-methyl-cyclohexanecarbonyl)-amino]-phenyl thiophene-2-yl-acetate of melting point 58° C.

Preparation of the Starting Material

Example (IV-a-1)

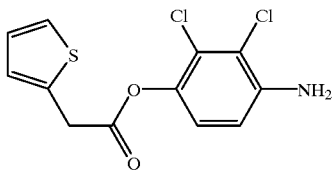

Process c)

Under an atmosphere of argon, 0.67 g (5.954 mmol) of potassium t-butoxide are added to a solution of 1.0 g (5,617 mmol) of 2,3-dichloro-4-hydroxyaniline in 30 ml of dimethylformamide, and the mixture is stirred for 5 hours. 0.9 g (5.617 mmol) of 2-thienylacetyl chloride are then added dropwise to this solution, and the mixture is stirred for a further 15 hours. The reaction mixture is poured into 300 ml of water and extracted 3 times with 100 ml of ethyl acetate each time. The combined organic phases are dried over magnesium sulphate and concentrated under reduced pressure. The residue is chromatographed over silica gel using cyclohexanelethyl acetate (5:1). This gives 0.55 g (33% of theory) of 4-amino-2,3-dichloro-phenyl thiophen-2-yl-acetate.

$^1$H-NMR (CDCl$_3$, TMS): δ=6.67 (d, 1H); 6.87 (d, 1H); 7.02 (m, 1H); 7.06 (m, 1H); 7.26 (m, 1H); ppm.

By the methods of Preparation Examples 1 and 2, and in accordance with the general description of the processes a) and b) according to the invention, the compounds of the general formula (Ia) listed in Table 1 below were obtained:

TABLE 1

(Ia)

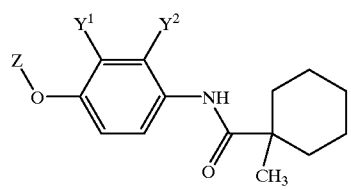

| Ex. No. | Y$^1$ | Y$^2$ | Z | phys. data |
|---|---|---|---|---|
| 3 | Cl | Cl | 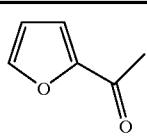 | m.p.: 161° C. |
| 4 | Cl | Cl | 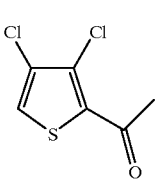 | m.p.: 75° C. |

TABLE 1-continued (Ia)

| Ex. No. | Y¹ | Y² | Z | phys. data |
|---|---|---|---|---|
| 5 | Cl | Cl | 2,5-dichloro-thiazol-4-yl carbonyl | m.p.: 62° C. |
| 6 | Cl | Cl | 3-benzyloxy-thiophen-2-yl carbonyl | NMR* 1.28; 1.37–1.72; 1.98–2.14; 2.30; 5.30, 6.86–8.47 |
| 7 | Cl | Cl | thiophen-2-yl carbonyl | m.p.: 115° C. |
| 8 | Cl | Cl | thiophen-3-yl carbonyl | m.p.: 126° C. |
| 9 | Cl | Cl | 5-chloro-thiophen-2-yl carbonyl | m.p.: 55° C. |
| 10 | Cl | Cl | 2,6-dichloro-5-fluoro-pyridin-3-yl carbonyl | m.p.: 55° C. |
| 11 | Cl | Cl | 2,6-dichloro-pyridin-4-yl carbonyl | m.p.: 120° C. |
| 12 | Cl | Cl | N-ethyl-N-isobutyl-methoxycarbonylamino | NMR*: 0.90; 1.25–2.15; 3.00–3.20; 4.95; 5.25–5.45; 6.90–8.30 |

TABLE 1-continued

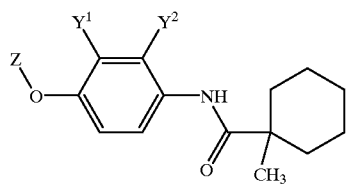

(Ia)

| Ex. No. | Y¹ | Y² | Z | phys. data |
|---|---|---|---|---|
| 13 | Cl | Cl | (ethyl N-methyl carbamate methyl ether) | NMR*: 1.10–1.70; 2.05; 3.03; 4.16 (t, 2H); 5.35; 6.95–8.30 |
| 14 | Cl | Cl | (4-acetyl-5-fluoro-1,3-dimethylpyrazole) | m.p.: 141–142° C. |
| 15 | Cl | Cl | (4-acetyl-1,3-dimethylpyrazole) | m.p.: 155° C. |
| 16 | Cl | Cl | (5-acetyl-4-trifluoromethyl-2-methylthiazole) | m.p.: 145° C. |
| 17 | Cl | Cl | (4-acetyl-3-trifluoromethyl-1-methylpyrazole) | m.p.: 169–173° C. |
| 18 | Cl | Cl | (acetyl methyl dihydrooxathiine) | m.p.: 111–113° C. |
| 19 | Cl | Cl | (2-acetyl-4,5-dibromothiophene) | m.p.: 145–146° C. |
| 20 | Cl | Cl | (5-acetyl-2-chloropyridine) | m.p.: 140° C. |

TABLE 1-continued

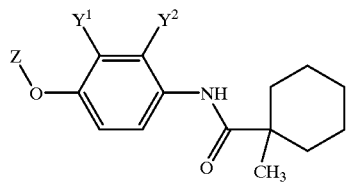

(Ia)

| Ex. No. | Y¹ | Y² | Z | phys. data |
|---|---|---|---|---|
| 21 | Cl | Cl | (2-acetyl tetrahydrofuran) | MS: M⁺ = 399 |
| 22 | Cl | Cl | (1-methyl-4-CF₃-3-C₂F₅-pyrazol-5-yl acetyl) | m.p.: 129–131° C. |
| 23 | Cl | Cl | (1-methyl-3-CHF₂-pyrazol-4-yl acetyl) | m.p.: 144–145° C. |
| 24 | Cl | Cl | (3,4-dichloroisothiazol-5-yl acetyl) | m.p.: 100–101° C. |

*) The ¹H NMR spectra were recorded in deuterochloroform (CDCl₃) or hexadeuterodimethyl sulfoxide (DMSO-d₆) using tetramethylsilane (TMS) as internal standard. Stated is the chemical shift as δ value in ppm.

By the method of Example (IV-a-1), and in accordance with the general description of the process c) according to the invention, the compounds of the general formula (IV-a) listed in Table 2 below were obtained:

TABLE 2

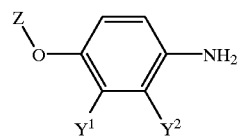

(IV-a)

| Ex. No. | Y¹ | Y² | Z | phys. data |
|---|---|---|---|---|
| IV-a-2 | Cl | Cl | (2-acetylbenzothiophene) | m.p.: 203–206° C. |
| IV-a-3 | Cl | Cl | (1-methylcyclohexyl acetyl) | m.p.: 68° C. |

TABLE 2-continued (IV-a)

| Ex. No. | Y¹ | Y² | Z | phys. data |
|---|---|---|---|---|
| IV-a-4 | Cl | Cl | (acetyl piperidine) | m.p.: 101° C. |
| IV-a-5 | Cl | Cl | (3,5-difluorobenzoyl) | m.p.: 140–142° C. |
| IV-a-6 | Cl | Cl | (acetyl, CH₃) | NMR*: 2.32 (s, 3H); 4.14 (s, 2H); 6.86 (d, 1H); 6.66 (d, 1H) |
| IV-a-7 | Cl | Cl | (2,6-dichloropyridin-4-yl carbonyl) | NMR*: 5.82 (s, 2H); 6.83 (d, 1H); 7.19 (d, 2H); 8.13 (s, 2H) |
| IV-a-8 | Cl | Cl | (5-fluoro-1,3-dimethylpyrazol-4-yl carbonyl) | NMR*: 2.32 (s, 3H); 3.70 (s, 3H); 5.71 (s, 2H); 6.80 (d, 1H); 7.06 (d, 1H) |
| IV-a-9 | Cl | Cl | (3-trifluoromethyl-1-methylpyrazol-4-yl carbonyl) | NMR*: 4.00 (s, 3H); 5.75 (s, 2H); 6.80 (d, 1H); 7.09 (d, 1H); 8.86 (s, 1H) |
| IV-a-10 | Cl | Cl | (4-trifluoromethyl-2-methylthiazol-5-yl carbonyl) | NMR*: 2.82 (s, 3H); 5.80 (s, 2H); 6.82 (d, 1H); 7.19 (d, 1H) |
| IV-a-11 | Cl | Cl | (1,3-dimethylpyrazol-4-yl carbonyl) | NMR*: 2.35 (s, 3H); 3.83 (s, 3H); 5.68 (s, 2H); 6.79 (d, 1H); 7.04 (d, 1H); 8.45 (s, 1H); |

*) The ¹H NMR spectra were recorded in deuterochloroform (CDCl₃) or hexadeuterodimethyl sulfoxide (DMSO-d₆) using tetramethylsilane (TMS) as internal standard. Stated is the chemical shift as δ value in ppm.

Use Examples

Example A

Botrytis Test (bean)/protective

| Solvent: | 4.7 parts by weight of acetone |
| --- | --- |
| Emulsifier: | 0.3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed to run-off point with the preparation of active compound. After the spray coating has dried on, 2 small pieces of agar overgrown with Botrytis cinerea are placed onto each leaf. The inoculated plants are placed in a dark moist chamber at 20° C. 3 days after the inoculation, the size of the diseased patched on the leaves is evaluated.

In this test, for example the following compounds of Preparation Examples (2), (3), (4), (5), (7), (8), (9), (12) and (13) exhibit, at an exemplary active compound concentration of 100 ppm, an efficacy of from 69 to 100%.

TABLE A

Botrytis Test (bean)/protective

| Active compound | Efficacy in % of the untreated control at a concentration of active compound of 100 ppm |
| --- | --- |
| 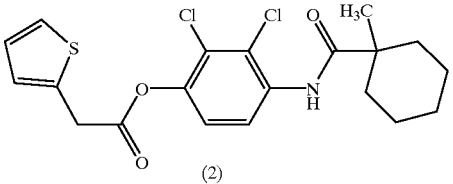 (2) | 100 |
| 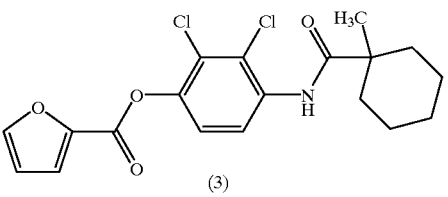 (3) | 97 |
| 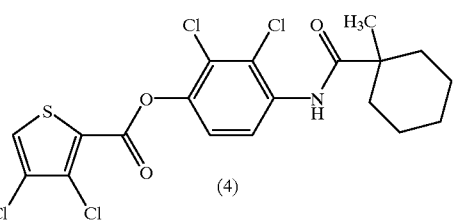 (4) | 100 |
| 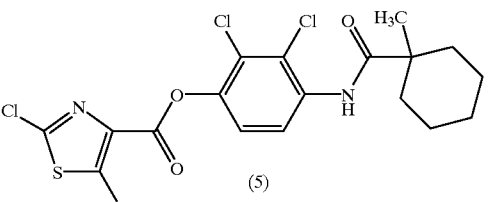 (5) | 97 |

TABLE A-continued

Botrytis Test (bean)/protective

| Active compound | Efficacy in % of the untreated control at a concentration of active compound of 100 ppm |
|---|---|
| (7) | 97 |
| (8) | 100 |
| (9) | 96 |
| (12) | 75 |
| (13) | 99 |

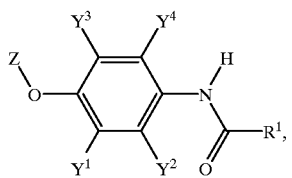

What is claimed is:

1. A compound of the formula (I)

(I)

wherein $Y^1$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^2$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^3$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, $Y^4$ represents hydrogen, halogen, alkyl, alkoxy, alkylthio having in each case 1 to 4 carbon atoms, halogenoalkyl, halogenoalkoxy, halogenoalkylthio having in each case 1 to 3 carbon atoms and 1 to 5 identical or different halogen atoms, wherein at least two of the substituents $Y^1$ to $Y^4$ represent halogen, $R^1$ represents in each case unsubstituted or mono- to pentasubstituted alkyl or alkenyl having in each case 4 to 10 carbon atoms, wherein the substituent is selected from the group consisting of halogen, alkoxy having 1 to 4 carbon atoms, alkylthio having 1 to 4 carbon atoms, halogenoalkoxy having 1 to 2 carbon atoms and 1 to 5 halogen atoms, halogenoalkylthio having 1 to 2 carbon atoms and 1 to 5 halogen atoms and unsubstituted or halogen- or alkyl-substituted cycloalkyl having 3 to 6 carbon atoms, wherein the carbon atom which is attached to the carbonyl group does not carry a hydrogen atom, or $R^1$ represents in each case unsubstituted or mono- to pentasubstituted cycloalkyl or cycloalkenyl having in each case 3 to 12 carbon atoms, wherein the substituent is selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 halogen atoms, halogenoalkoxy having 1 to 2 carbon atoms and 1 to 5 halogen atoms, halogenoalkylthio having 1 to 2 carbon atoms and 1 to 5 halogen atoms and unsubstituted or halogen- or alkyl-substituted cycloalkyl having 3 to 6 carbon atoms, and Z represents Het-A

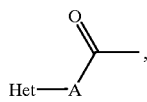

wherein
Het represents heterocyclyl having 3 to 7 ring members, 1 to 3 of which is in each case identical or different hetero atoms selected from the group consisting of nitrogen, oxygen and sulphur, which is unsubstituted or mono- to trisubstituted by halogen, alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl having in each case 1 to 4 carbon atoms, A represents a single bond, oxygen, sulphur, alkanediyl having 1 to 2 carbon atoms, or represents

wherein
$R^5$ represents hydrogen or alkyl having 1 to 4 carbon atoms, and
Q represents oxygen.

2. The compound of claim 1 wherein $Y^1$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethyoxy, difluoromethylthio, difluorochloromethylthio, trifluoromethylthio, $Y^2$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, difluoromethylthio, difluorochloromethylthio, trifluoromethylthio, $Y^3$ represents hydrogen, fluorine, chlorine, bromine, methyl, methoxy, ethoxy, methylthio, ethylthio, trifluoromethyl, difluorormethyl, fluoromethyl, fluorochloromethyl, difluoromethoxy, trifluoromethoxy, difluorochloromethoxy, difluoromethylthio, difluorochloromethylthio, trifluoromethylthio, $Y^4$ represents hydrogen, fluorine, chlorine, bromine, methyl, methoxy, ethoxy, methylthio, ethylthio, trifluoromethyl, difluoromethyl, fluoromethyl, fluorochloromethyl, difluoromethoxy, trifluoromethoxy, difluorochloromethoxy, dilfuorormethylthio, difluorochloromethylthio, trifluoromethylthio, where at least two of the radicals $Y^1$ to $Y^4$ in each case represent fluorine, chlorine or bromine, $R^1$ represents 1-methyl-propyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the alkyl radical is unsubstituted or substituted by 1 to 3 halogen atoms, selected from the group consisting of fluorine, chlorine and bromine, or $R^1$ represents 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl4-pentenyl, 2-methyl-4-pentenyl, 3-methylpentenyl, 4-methylApentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-1-methyl-2-propenyl, 1-ethyl-2-methyl-1-propenyl and 1-ethyl-2-methyl-2-propenyl, wherein the alkyl radical is unsubstituted or substituted by 1 to 3 halogen atoms, selected from the group consisting of fluorine, chlorine and bromine, or $R^1$ represents cyclopropyl, cyclobutyl, cyclopentyl, cyclohexyl, cycloheptyl, 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl, wherein the radical is unsubstituted or substituted by 1 to 3 halogen atoms, selected from the group consisting of chlorine, fluorine, bromine, methyl and ethyl, or $R^1$ represents bicyclo-[2.2 1]-hex-5-yl, bicyclo-[2.2.1]-hept-2-yl, bicycylo-[2.2.2]-oct-2-yl, bicyclo-[3.2.1]-oct-6-yl, bicyclo-[3.2.2]-non-6-yl, bicyclo-[4.2.2]-dec-7-yl, bicyclo-[3.1.0]-hex-1-yl, bicyclo-[4.1.0]-hept-1-yl, bicyclo-[4.3.0]-non-1-yl, bicyclo-[4.4.0]-dec-1-yl, particularly preferably represents 5-methyl-bicyclo-[2.1.1]-hex-5-yl, 2-methyl-bicyclo-[2.2.1]-hept-2-yl, 2-methyl-bicyclo-[2.2.2]-oct-2-yl, 6-methyl-bicyclo-[3.2.1]-oct-6-yl, 6-methyl-bicyclo-[3.2.2]-non-6-yl, 7-methyl-bicyclo-[4.2.2]-dec-7-yl, 1-methyl-bicyclo-[3.1.0]-hex-1-yl, 1-methyl-bicyclo-[4.1.0]-hept-1-yl, 1-methyl-bicyclo-[4.3.0]-non- 1-yl, 1-methyl-bicyclo-[4.4.0]-dec-1-yl, 2-methyl-bicyclo-[3.1.0]-hex-1-yl, 2-methyl-bicyclo-[4.1.0]-hept-1-yl, 2-methyl-bicyclo-[4.3.0]-non-1-yl, 2-methyl-bicyclo-[4.4.0]-dec-1-yl, bicyclo-[2.2.1]-hept-2-en-5-yl, bicyclo-[2.2.2]-oct-2-en-5-yl, bicyclo-[4.2.2]-dec-7-en-2-yl, bicyclo-14.3.0]-non-7-en-1-yl, bicyclo-[4.4.0]dec-3-en-1-yl, bicyclo-[4.1.0]-hept-3-en-1-yl, 5-methyl-bicyclo-[2.2.1]-hept-2-en-5-yl, 5-methyl-bicyclo-[2.2.2]-oct-2-en-5-yl, 2-methyl-bicyclo-[4.2.2]-dec-7-en-2-yl, 2-methyl-bicyclo-[4.3.0]-non-7-en-1-yl, 2-methyl-bicyclo-[4.4.0]-dec-3-en-1-yl and 2-methyl-bicyclo-[4.1.0]-hept-3-en-1-yl, Z represents a grouping $$\underset{\text{Het}-\text{A}}{\overset{Q}{\diagup\!\!\!\diagdown}}\,,$$

wherein

Het represents heterocyclyl having 3 to 7 ring memebers, 1 to 3 of which are in each case identical or different hetero atoms, selected from the group consisting of nitrogen, oxygen and sulphur, which is unsubstituted or mono- to trisubstituted by halogen, alkyl, alkoxy, alkylthio, alkylsulphinyl, alkylsulphony, halogenoalkyl, halogenoalkoxy, halogenoalkylthio, halogenoalkylsulphinyl or halogenoalkylsulphonyl having in each case 1 to 4 carbon atoms, A represents the single bond, oxygen, sulphur, methylene or represents $$\underset{|}{\overset{R^5}{\diagdown\!\!\!\diagup}}\mathrm{N}\diagdown\,,$$

wherein $R^5$ represents hydrogen, methyl or ethyl, and

Q represents oxygen.

3. A pesticide, comprising at least one compound of claim 1 and one or more extenders and/or surfactants.

4. A method of controlling pests, comprising the step of applying the compound of claim 1 on pests and/or their habitat.

5. A process for preparing a pesticide, comprising the step of mixing the compound of claim 1 with extenders and/or surfactants.

6. A process for preparing the compound of claim 1, comprising the step of reacting a hydroxyl compound of a) the general formula (II)

(II)

wherein $R^1$, $Y^1$, $Y^2$, $Y^3$ and $Y^4$ are each as defined in claim 3 with a halogen compound of the general formula (III)

$$Z-X^1 \qquad\qquad\text{(III),}$$

wherein

Z is as defined in claim 3 and $X^1$ represents halogen, or b) reacting an amino compound of the general formula (IV)

(IV)

wherein $Y^1$, $Y^2$, $Y^3$, $Y^4$ and Z are each as defined in claim 3 with a carboxylic acid derivative of the general formula (V)

(V)

wherein $R^1$ is a defined in claim 3 and $X^2$ represents halogen or
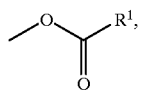
7. A compound of the formula (IV-a)
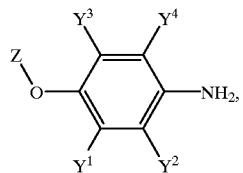
(IV-a)
wherein
$Y^1$, $Y^2$, $Y^3$, $Y^4$ and Z are each as defined in claim 3, but where at least two of the radicals $Y^1$, $Y^2$, $Y^3$ or $Y^4$ represent halogen.
8. A compound of the formula
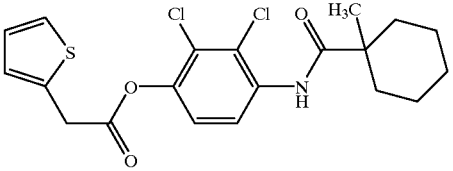
* * * * *